United States Patent [19]
Pacifici et al.

[11] Patent Number: 4,503,268
[45] Date of Patent: Mar. 5, 1985

[54] PREPARATION OF MONOCHLOROHYDROQUINONE

[75] Inventors: James G. Pacifici; Allen J. Blankenship, both of Batesville, Ark.

[73] Assignee: Eastman Kodak Company, Rochester, N.Y.

[21] Appl. No.: 551,760

[22] Filed: Nov. 14, 1983

[51] Int. Cl.$^3$ .................. C07C 39/08; C07C 39/24
[52] U.S. Cl. .................................... 568/765; 568/779
[58] Field of Search ................................ 568/765, 779

[56] References Cited

U.S. PATENT DOCUMENTS 3,927,125 12/1975 Grinev et al. ..................... 568/765
3,931,340 1/1976 Nishihara et al. ................. 568/765

Primary Examiner—Werren B. Lone
Attorney, Agent, or Firm—Clyde L. Tootle; J. Frederick Thomsen; Daniel B. Reece, III

[57] ABSTRACT

Disclosed is a process for the preparation of monochlorohydroquinone by treating hydroquinone in hydrochloric acid with chlorine at 100° to 105° C.

2 Claims, No Drawings

PREPARATION OF MONOCHLOROHYDROQUINONE

DESCRIPTION

The invention concerns a novel process for the preparation of monochlorohydroquinone.

Several methods for the preparation of monochlorohydroquinone have been described in the prior art such as U.S. Pat. Nos. 1,912,744, 2,748,173 and 3,959,392, Japanese Published Application No. 81-45,433 (Chemical Abstracts 95:80474g) and J. prakt. Chem., 104, 84–4 (1922). Each of these known processes is economically or technically disadvantageous in that it requires the use of superatmospheric conditions, employs benzoquinone as the starting material, produces an unacceptably high amount of polychlorinated hydroquinone, produces tar-like by-products which cause the product to be discolored, or gives poor conversion of hydroquinone. Thus, these prior art processes are not entirely suitable for preparing monochlorohydroquinone containing relatively low amounts of starting material and polychlorohydroquinone.

We have discovered that monochlorohydroquinone can be prepared by treating hydroquinone with chlorine in hydrochloric acid at a temperature of 100° to 105° C. Carrying out the reaction at 100° to 105° C. is important since the use of lower temperatures results in the formation of a black, tarry material of no practical utility. We have also found that the hydrochloric acid reaction material should contain at least one mole of hydrogen chloride per mole of hydroquinone reactant. While a molar excess of hydrogen chloride, e.g. a hydrogen chloride:hydroquinone ratio as high as five, may be used there normally is no advantage to do so.

Our invention is further illustrated by the following examples.

EXAMPLE 1

To a 1-liter flask was charged 200 ml of 36 percent hydrochloric acid and 110 g (1.0 m) of hydroquinone. The slurry was heated to 105° C., with agitation, until complete solution occurs. To the clear solution was added 72 g (1.0 mole) of chlorine over 40 minutes. Upon addition of chlorine, the reaction mixture was cooled slowly to 25°–30° C. and a seed crystal added to induce crystallization. After crystallization occurred, the reaction mixture was cooled to 10°–15° C. and filtered. The filter cake was dried at 50° C. under vacuum for 15 hours. Isolated was 137.7 g of crude product. Gas chromatography (GC) analysis of the crude product gave the following results:

% Hydroquinone: 8.6
% Monochlorohydroquinone: 75.1
% Dichlorohydroquinone 12.1

EXAMPLES 2-9

The procedure of Example 1 was repeated using the same volume of water or concentrated hydrochloric acid and various chlorination temperatures. The results, as determined by GC analysis, obtained are shown in Table I.

TABLE I

| Ex. No. | % HCl | Temp., °C. | % HQ | % ClHQ | % Cl$_2$HQ |
|---|---|---|---|---|---|
| 2 | 0 | 25–30 | (Composition of black, tarry, | | |
| 3 | 0 | 90–100 | crude product not determined.) | | |
| 4 | 36 | 5–10 | 43.1 | 5.8 | 43.3 |
| 5 | 36 | 60–65 | 24.2 | 54.7 | 11.9 |
| 6 | 36 | 80–85 | 14.0 | 67.0 | 14.7 |
| 7 | 36 | 100–105 | 12.9 | 75.6 | 10.2 |
| 8 | 36 | 100–105 | 10.5 | 74.6 | 11.2 |
| 9 | 36 | 100–105 | 12.2 | 74.3 | 11.7 |

EXAMPLE 10

To a 500-ml flask was charged 50 g of 36% hydrochloric acid, 50 g of water and 55 g (0.5 mole) hydroquinone. The slurry was heated to 105° C. with agitation, until complete solution occurs. To the clear solution was added 36 g (0.5 mole) of chlorine over 40 minutes. Upon completion of the chlorine addition the reaction mixture was cooled to 15° C. and the product crystallized. Isolated was 50.0 g (69.3%) of product with the following assay:

% Hydroquinone: 10.5
% Monochlorohydroquinone: 74.6
% Dichlorohydroquinone: 11.2

The filtrate was partially stripped under vacuum and cooled. A second crop of product (14.6 g) was isolated which assayed 55.2% monochlorohydroquinone, 22.1% hydroquinone and 6.3% dichlorohydroquinone.

The invention has been described in detail with particular reference to preferred embodiments thereof, but it will be understood that variations and modifications can be effected within the spirit and scope of the invention.

We claim:

1. Process for the preparation of monochlorohydroquinone which comprises treating hydroquinone with chlorine in hydrochloric acid at a temperature of 100° to 105° C.

2. Process according to claim 1 wherein the hydrochloric acid contains at least one mole hydrogen chloride per mole of hydroquinone.